United States Patent
Umezawa et al.

(10) Patent No.: US 7,169,614 B2
(45) Date of Patent: Jan. 30, 2007

(54) ELECTROCHEMICAL DETECTION METHOD OF COMPLEMENTARITY TO NUCLEIC ACID BASES

(75) Inventors: Yoshio Umezawa, Tokyo (JP); Hiroshi Aoki, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 324 days.

(21) Appl. No.: 10/471,657

(22) PCT Filed: Mar. 13, 2001

(86) PCT No.: PCT/JP01/01974

§ 371 (c)(1),
(2), (4) Date: Nov. 18, 2003

(87) PCT Pub. No.: WO02/073183

PCT Pub. Date: Sep. 19, 2002

(65) Prior Publication Data

US 2005/0153285 A1    Jul. 14, 2005

(51) Int. Cl.
G01N 33/00 (2006.01)
C12M 3/00 (2006.01)
C07H 21/04 (2006.01)
C02F 1/00 (2006.01)
B32B 27/04 (2006.01)
B01D 59/42 (2006.01)

(52) U.S. Cl. .................. 436/94; 435/6; 435/287.2; 536/23.1; 210/746; 422/98; 204/527

(58) Field of Classification Search .................. 435/6, 435/287.2; 436/94; 536/23.1, 24.31; 204/543
See application file for complete search history.

(56) References Cited

U.S. PATENT DOCUMENTS 6,221,586 B1 *  4/2001  Barton et al. .................. 435/6

FOREIGN PATENT DOCUMENTS

JP    2001-56311    2/2001

OTHER PUBLICATIONS

Hianik, T. et al., "The Changes in Dynamics of Solid Supported Lipid Films Following Hybridization of Short Sequence DNA", Electroanalysis 2000, vol. 12, No. 7, pp. 495-501.
Patolsky, F. et al., "Electrochemical Transduction of Liposome-Amplified DNA Sensing", Angewandte Chemie International Edition in English, 2000, vol. 39, No. 5, pp. 940-943.
Patolsky, F., et al., "Electronic Transduction of DNA Sensing Processes on Surfaces: Amplification of DNA Detection and Analysis of Single-Base Mismatches by Tagged Liposomes", Journal of American Chemical Society, 2001, vol. 123, pp. 5194-5205.

(Continued)

*Primary Examiner*—Bradley L. Sisson
(74) *Attorney, Agent, or Firm*—Wenderoth, Lind & Ponack, L.L.P.

(57) ABSTRACT

A convenient and commonly applicable method for the specific detection of a nucleic acid with an arbitrary sequence is provide. This method comprises attaching at least a nucleic acid single strand to an electrode, bringing the thus-obtained modified electrode in contact with a solution containing the analyte single-stranded nucleic acid, and measuring the redox reaction of the redox marker.

12 Claims, 6 Drawing Sheets

OTHER PUBLICATIONS

Patolsky, F., et al., "Electronic Transduction of Polymerase or Reverse Transcriptase Induced Replication Processes on Surfaces: Highly Sensitive and Specific Detection of Viral Genomes", Angewandte Chemie International Edition in English, 2001, vol. 40, No. 12, pp. 2261-2265.

Patolsky, F., et al., "Detection of Single-Base DNA Mutations by Enzyme-Amplified Electronic Transduction", Nature Biotechnology, Mar. 2001, vol. 19, pp. 253-257.

Patolsky, F., et al., "Redox-Active Nucleic-Acid Replica for the Amplified Bioelectrocatalytic Detection of Viral DNA", Journal of the American Chemical Society, 2002, vol. 124, No. 5, pp. 770-772.

Lee, T., et al., "Direct DNA Hybridization Detection Based on the Oligonucleotide-Functionalized Conductive Polymer", Analytical Chemistry, Nov. 2001, vol. 73, No. 22, pp. 5629-5632.

Korri-Youssoufi, H., et al., "Electrochemical Biosensing of DNA Hybridization by Ferrocenyl Groups Functionalized Polypyrrole", Analytic Chimica Acta, 2002, vol. 469, pp. 85-92.

Thompson, L., et al., "Label-Free DNA Hybridization Probe Based on a Conducting Polymer", Journal of the American Chemical Society, 2003, vol. 125, pp. 324-325.

Boon, E., "Mutation Detection by Electrocatalysis at DNA-Modified Electrodes", Nature Biotechnology, Oct. 2000, vol. 18, pp. 1096-1100.

Erdem, A., et al., "Novel Hybridization Indicator Methylene Blue for the Electrochemical Detection of Short DNA Sequences Related to the Hepatitis B Virus", Analytica Chimica Acta, 2000, vol. 422, pp. 139-149.

Maruyama, K., et al., "Electrochemical and DNA-Binding Properties of Dipyridophenazine Complexes of Osmium (II)", Journal of Electroanalytical Chemistry, 2001, vol. 510, pp. 96-102.

Maruyama, K., et al., "DNA Sensor with a Dipyridophenazine Complex of Osmium (II) as an Electrochemical Probe", Analytical Chemistry, Aug. 2002, vol. 74, pp. 3698-3703.

Xu, C., et al., "Electrochemical Labeled DNA Probe for the Detection of Sequence-Specific DNA", Analytica Chimica Acta, 2000, vol. 411, pp. 31-36.

Cai, H., et al., "Colloid Au-Enhanced DNA Immobilization for the Electrochemical Detection of Sequence-Specific DNA", Journal of Electroanalytical Chemistry, 2001, vol. 510, pp. 78-85.

Nakayama, M., et al., "DNA Sensors Using a Ferrocene-Oligonucleotide Conjugate", Talanta, 2002, vol. 56, pp. 857-866.

Anne, A., et al., "3'-Ferrocene-Labeled Oligonucleotide Chains End-Tethered to Gold Electrode Surfaces: Novel Model Systems for Exploring Flexibility of Short DNA Using Cyclic Voltammetry", Journal of the American Chemical Society, 2003, vol. 125, pp. 1112-1113.

Saghatelian, A., et al., "DNA Detection and Signal Amplification via an Engineered Allosteric Enzyme", Journal of the American Chemical Society, 2003, vol. 125, pp. 344-345.

Wang, J., et al., "Metal Nanoparticle-Based Electrochemical Stripping Potentiometric Detection of DNA Hybridization", Analytical Chemistry, Nov. 2001, vol. 73, No. 22, pp. 5576-5581.

Wang, J. et al., "Silver-Enhanced Colloidal Gold Electrochemical Stripping Detection of DNA Hybridization", Langmuir, 2001, vol. 17, pp. 5739-5741.

Wang, J., et al., "Magnetically-Induced Solid-State Electrochemical Detection of DNA Hybridization", Journal of the American Chemical Society, 2002, vol. 124, pp. 4208-4209.

Wang, J., et al., ""Electroactive Beads" for Ultrasensitive DNA Detection", Langmuir, 2003, vol. 19, pp. 989-991.

Wang, J., et al., "Particle-Based Detection of DNA Hybridization Using Electrochemical Stripping Measurements of an Iron Tracer", Analytica Chimica Acta, 2003, vol. 482, pp. 149-155.

Wang, J., "Electrochemical Coding Technology for Simultaneous Detection of Multiple DNA Targets", Journal of the American Chemical Society, 2003, vol. 125, pp. 3214-3215.

A. Erden, "Novel Hybridization Indicator Methylene Blue for the Electrochemical Detection of Short DNA Sequences Related to the Hepatitis B Virus", Analytica Chimica Acta, vol. 422, No. 2, Oct. 12, 2000, pp. 139-149.

A. B. Steel, "Electrochemical Quantitation of DNA Immobilized on Gold", Analytical Chemistry, vol. 70, No. 22, Nov. 15, 1998, pp. 4670-4677.

J. Wang, "Peptide Nucleic Acid Probes for Sequence-Specific DNA Biosensors", Journal of the American Chemical Society, vol. 118, No. 2, Aug. 21, 1996, pp. 7667-7670.

* cited by examiner

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 1
cagtgcctca                                                            10

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 2
ggcagtgcct cacaa                                                      15

<210> SEQ ID NO 3
<211> LENGTH: 15
<212> TYPE: DNA
<213> ORGANISM: Artificial Sequence
```

-continued

```
<220> FEATURE:
<223> OTHER INFORMATION: Description of Artificial Sequence: Synthesized
      Oligonucleotide

<400> SEQUENCE: 3
ttgtgaggca ctgcc                                                       15

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 4
tgaggcactg                                                             10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 5
tgagacactg                                                             10
```

ELECTROCHEMICAL DETECTION METHOD OF COMPLEMENTARITY TO NUCLEIC ACID BASES

This application is a U.S. national stage of International Application No. PCT/JP01/01974 filed Mar. 13, 2001.

TECHNICAL FIELD

The present invention relates to a method for electrochemical detection of nucleobase pair complementarity. More specifically, the present invention relates to a method of determining the sequence of an analyte nucleic acid by electrochemically detecting its base pair complementation to a probe nucleic acid bonded to an electrode.

BACKGROUND ART

In recent years, with the technical progress in the field of molecular biology, genome structures of various organisms are being revealed. Further, the elucidation of genome structures has revealed that gene mutations participate in various genetic and viral diseases. Accordingly, in various fields of medicine, forensic medicine, molecular biology and the like, the establishment of a method for detecting and analyzing specific gene sequences and mutations in gene sequences has become an important task.

Until now, various methods for detecting and analyzing gene mutations through spectroscopic, biochemical or electrochemical means have been studied. Presently, in general, electrophoresis and high-performance liquid chromatography (HPLC) are applied to detect and analyze gene mutations. However, both of these conventional methods were problematic in that simultaneous analysis of a large number of samples is difficult, that the analysis itself is time-consuming, and that the accuracy is not high.

In recent years, an electrochemical measurement method, which possesses high measuring accuracy and enables detection with trace amounts of reagents as well as simultaneous analysis of many samples, has attracted much interest, and various modified electrodes have been studied and reported as a biosensor (Wang, J., *Anal. Chem.* 1999, 71, 328).

Specifically, initially, an enzyme electrode comprising an enzyme immobilized on the surface of an electrode as a film, which enables detection by converting changes in substances into electric signals by enzyme reaction, was reported. However, in order to apply this method to the detection and analysis of genes, an enzyme that specifically reacts with the desired analyte (target gene) had to be selected, making its applicability low and problematic.

Hence, recently, DNA biosensors which detect hybridization between probes immobilized on the electrode and target genes as electric signals are being intensely studied. For example, Patolsky et al. have reported immobilizing biotinylated oligonucleotide probes on gold electrodes through phosphothiolate groups, and allowing the probe and the target single-stranded DNA to be in contact, thereby forming a hybrid; further, an enzyme to which avidin that specifically interact with biotin is bonded to is reacted therewith and DNA is detected from the electric signal emitted by the enzyme reaction (*Langmuir*, 1999, 15, 3703). However, this method requires a large number of procedures such as probe immobilization, hybridization, protein interaction, enzyme reaction and deposition of the product onto electrodes, and thus could not be called a simple method.

Further, Takenaka et al. have reported a method in which DNA is detected by a naphthalene-ferrocene redox intercalator using an oligonucleotide probe chemisorbed onto gold electrodes via a thiol anchor (*Anal. Chem.* 2000, 72, 1334). However, although it in generally possible to distinguish between single-stranded DNA and double-stranded DNA in methods that use an intercalator as the electrode-active probe, because the binding region of the intercalator is sequence-dependent, the method was problematic in that an intercalator that corresponds to the analyte had to be selected.

Furthermore, De Lumley-Woodyear et al. reported a method in which enzyme (HRP)-labeled $(dT)_{25-30}$ or $(dA)_{25-30}$ is covalently attached to a conductive redox polymer film formed on a glassy carbon electrode, and electric signals based on the enzyme reaction caused by its hybridization with complementary oligonucleotides are detected (*Anal. Chem.* 1999, 71, 394). However, such methods that use enzyme-labeling require intricate procedures when labeling the oligonucleotide with an enzyme, and the excess enzyme has to be removed by cleansing, causing problems in that the measuring accuracy is not necessarily stable.

The present invention has been achieved under the foregoing circumstances, and its object is to provide, upon solving the problems associated with the prior art, a simple, highly applicable method for specifically detecting a nucleic acid with an arbitrary sequence.

DISCLOSURE OF INVENTION

In order to solve the foregoing problems, the present invention firstly provides a method for electrochemical detection of nucleobase pair complementarity, which comprises contacting a modified electrode obtained by bonding at least a singlestranded nucleic acid to an electrode, with a solution containing an analyte single-stranded nucleic acid and a redox marker; and detecting the disappearance of the electric signal generated by the reaction between the modified electrode and the redox marker, when the single stranded nucleic acid on the modified electrode and the analyte single stranded nucleic acid are complementary.

The present invention secondly provides the method for electrochemical detection of nucleobase pair complementarity, wherein the electrode is a gold disk electrode.

Further, the present invention provides thirdly the method for electrochemical detection of nucleobase pair complementarity, wherein a molecule that does not show complementarity to the analyte single-stranded nucleic acid is bonded to the modified electrode along with the single-stranded nucleic acid; fourthly, the method for electrochemical detection of nucleobase pair complementarity, wherein the single-stranded nucleic acid and the molecule that does not show complementarity to the analyte single-stranded nucleic acid form a mixed monolayer on the surface of the electrode; and fifthly, the method for electrochemical detection of nucleobase pair complementarity, wherein the molecule that does not show complementarity to the analyte single-stranded nucleic acid is 6-mercapto-1-hexanol.

As embodiments, the present invention provides sixthly, any of the method for electrochemical detection of nucleobase pair complementarity, wherein the single-stranded nucleic acid is a single-stranded peptide nucleic acid; and seventhly, any of the method for electrochemical detection of nucleobase pair complementarity, wherein the concentration of the analyte single-stranded nucleic acid is $10^{-11}$ to $10^{-2}$ M.

In addition, as further embodiments, the present invention eighthly provides any of the method for electrochemical detection of nucleobase pair complementarity, wherein the analyte single-stranded nucleic acid is a single-stranded DNA.

The present invention provides ninthly, the method for electrochemical detection of nucleobase pair complementarity, wherein a water-soluble redox marker $[Fe(CN)_6]^{4-/3-}$, instead of an intercalator, is used; and tenthly, the method for electrochemical detection of nucleobase pair complementarity, wherein the concentration of $[Fe(CN)_6]^{4-/3-}$ is 0.1 to 1 mM.

In addition, the present invention eleventhly provides the method for electrochemical detection of nucleobase pair complementarity, wherein the redox reaction is measured by voltammetry.

Furthermore, the present invention twelfthly provides a modified electrode for detecting nucleobase pair complementarity by the method of any one of claims 1 to 11, which comprises a mixed monolayer of a peptide nucleic acid and a molecule that does not show complementarity to the analyte nucleic acid, formed on the surface of a gold disk electrode.

BEST MODE FOR CARRYING OUT THE INVENTION

The present invention relates to a method for electrochemical detection of nucleobase pair complementarity. Specifically, it may be described as a detection method that uses a so-called ion-channel sensor, which is based on the principle that when an analyte binds to a receptor immobilized on the surface of an electrode and the electron transfer of the redox maker to the electrode is suppressed physically and/or electrostatically, the electron transfer between the redox marker and the electrode is inhibited, leading to the appearance of electric signals.

Regarding ion-channel sensors, a large number of reports have been made since its proposal by the present inventors in 1987. For example, methods for detecting hydrogen ions (*Electroanalytical Chemistry* Vol. 19. Marcel Dekker, New York, 1996, p. 109; *J. Am. Chem. Soc.* 1997, 119, 8720), antibodies (*Langmuir,* 1997, 13, 1783) and the like with ion-channel sensors have been reported so far. Further, the present inventors have also reported a method for detecting various ions and molecules such as metal cations (*Anal. Chem.* 1987, 59, 2842; *J. Electroanal. Chem.* 1996, 401, 65; *Mikrochim. Acta,* 1999, 132, 55), nucleotides (*Thin Solid Films* 1989, 180, 129; *Anal. Chem.* 1990, 62, 1252, etc.), inorganic anions (*Anal. Chem.* 1999, 71, 1183) and amines (*J. Electroanal. Chem.* 1999, 473, 105) using ion-channel sensors. Moreover, the present inventors have clarified that selective detection of highly hydrophilic phosphate and detection of polyions such as protamine (*Anal. Chem.* 1999, 71, 5109) and heparin (*Anal. Chem. Acta* 2000, 411, 163) are possible by using ion-channel sensors.

Therefore, based on such knowledge, the present inventors have focused on the fact that nucleic acids such as DNA are polyions like the protamine and heparin, and studied the use of ion-channel sensors in the detection and analysis of nucleic acids. And as a result of assiduous studies, the present invention has been achieved.

Figure 1:
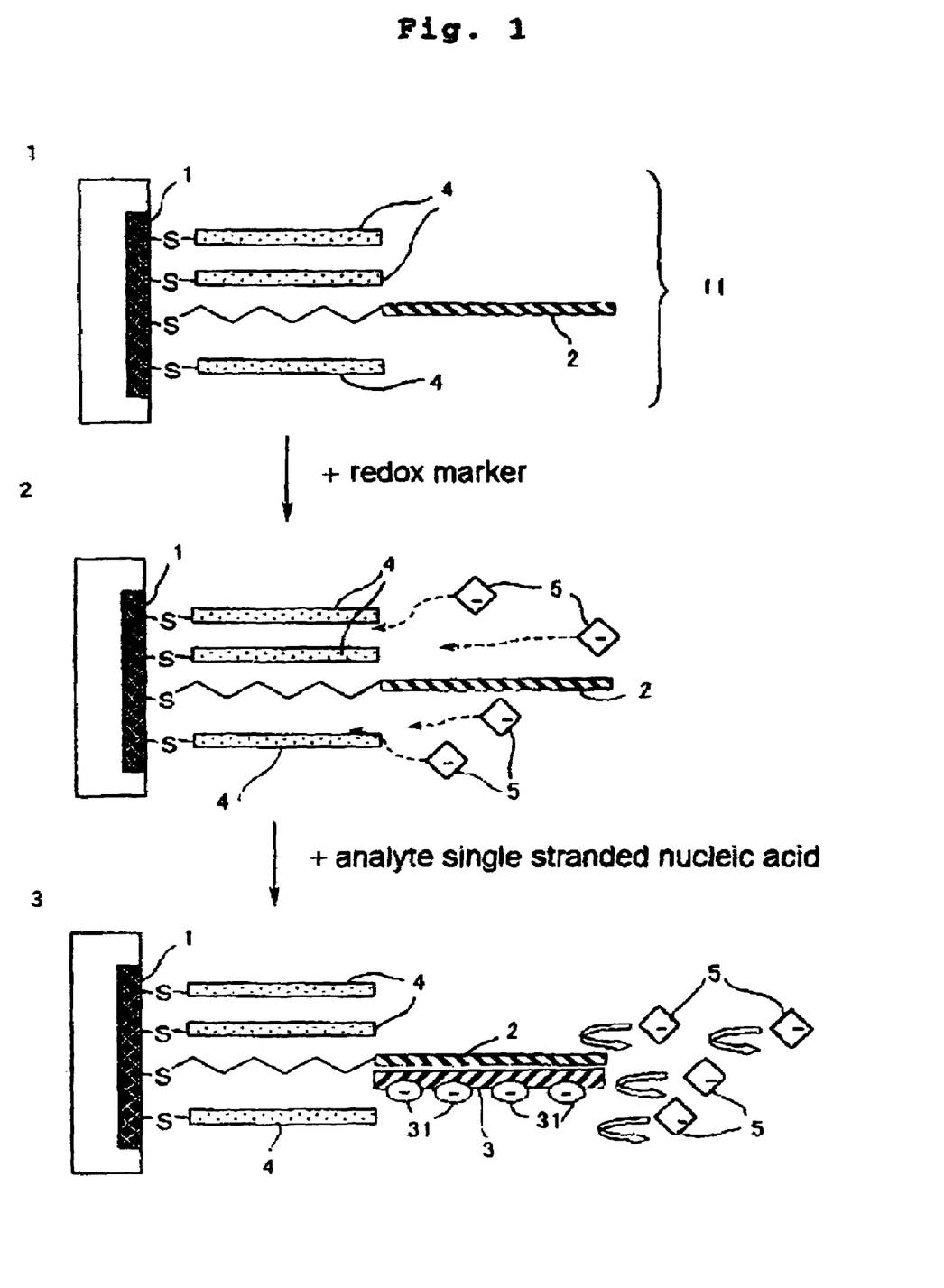
FIG. 1 is a schematic view showing the outline of the method for electrochemical detection of nucleobase pair complementarity of the present invention (1: electrode, 2: (probe) single-stranded nucleic acid, 3: analyte single-stranded nucleic acid, 4: molecules filling space between probe molecules, 5: redox marker, 11: modified electrode).

That is, the method for electrochemical detection of nucleobase pair complementarity of the present invention comprises: forming a modified electrode by linking a single-stranded nucleic acid to an electrode; contacting this modified electrode with a solution containing an analyte nucleic acid for which its complementarity to the single-stranded nucleic acid is to be confirmed and a redox marker; and detecting the disappearance of the electric signal generated by the reaction between the modified electrode and the redox marker, when the single stranded nucleic acid on the modified electrode and the analyte single stranded nucleic acid are complementary. In order to describe the method for electrochemical detection of nucleobase pair complementarity of the present invention more specifically, a scheme is shown in FIG. 1.

That is, in the present invention, at least a single-stranded nucleic acid (2) is linked to an electrode (1), and the resulting electrode is used as a modified electrode (11) (step 1). The single-stranded nucleic acid (2) linked to the electrode (1) functions as a probe molecule, and when the analyte single-stranded nucleic acid (3) in the solution shows complementarity to this single-stranded nucleic acid probe (2), hybridization between the complementary nucleic acids occurs on the electrode (1) (step 3). Such hybridization not only makes it difficult for the redox marker (5) in the solution to physically access the electrode, but the negative charge (31) on the surface of the analyte single-stranded nucleic acid (3) also hinders electron transfer from the redox marker (5).

Meanwhile, when the analyte single-stranded nucleic acid (3) does not exhibit complementarity to the single-stranded nucleic acid probe (2) on the electrode (1) (step 2), electron transfer from the redox marker (5) is not hindered, so that the electrode reaction proceeds smoothly. Therefore, by comparing the redox potential of the redox marker (5) in a solution containing only the redox marker (5) and not containing the analyte single-stranded nucleic acid (3) with the redox potential of the redox marker (5) in a solution that also contains the analyte single-stranded nucleic acid (3), whether the analyte single-stranded nucleic acid (3) is complementary to the probe single-stranded nucleic acid (2) on the electrode (1) or not can be clarified.

In the present invention, the material of the electrode (1) is not particularly limited as long as the single-stranded nucleic acid (2) that acts as a probe can be linked to it. Preferable is a gold electrode, for which a chemisorption method through a sulfur atom or the like is established. Further, the shape of the electrode (1) is not particularly limited either. However, as will be described later, since it is preferable that the probe single-stranded nucleic acid (2) on the electrode (1) is in the form of a monolayer with some space between the molecules, a disk electrode is desirable. Here, the electrode area of the disk electrode is not particularly limited. Nevertheless, in order to measure even a small amount of analyte in high accuracy, it is preferable that the electrode area is less than 5 mm$^2$.

In the method for electrochemical detection of nucleobase pair complementarity of the present invention, the single-stranded nucleic acid probe (2) may be singly linked to the surface of the electrode (1), or molecules (4) that fill the space between the probe molecules and adjusts the molecular space between the single-stranded nucleic acid probes (2) may also be linked thereto. This is because, as shown in the after-mentioned Examples, it is preferable that the single-stranded nucleic acid probes (2) are vertically oriented on the electrode to form monolayers. In other words, when the single-stranded nucleic acid probes (2) are deposited on the electrode (1) too tightly, the analyte single-stranded nucleic acid (3) may not be able to insert itself between the single-stranded nucleic acid probes (2), preventing sufficient hybridization. On the other hand, shortening the incubation time for the purpose of creating spaces between the monolayers of the single-stranded nucleic acid probes (2) may prohibit the single-stranded nucleic acid probes (2) to orient vertically, and cause them to lie down on the surface of the electrode (1), preventing sufficient hybridization.

Accordingly, the present inventors have found, through assiduous studies, that in order to fill the void between the molecules on the electrode (1) and adjust the molecular spaces between the single-stranded nucleic acid probes (2) to expedite the hybridization of the single-stranded nucleic acid probes (2) to the analyte nucleic acids (3), it is effective to orient the analyte single-stranded nucleic acids (3) vertically on the electrode (1), and prevent them from lying down by linking molecules (4) that fill the space between the probe molecules along with the single-stranded nucleic acids (2) to form a mixed monolayer.

Such molecules (4) that fill the space between the probe molecules are not particularly limited as long as they are non-complementary to the analyte single-stranded nucleic acid (3) and can be stably linked to the electrode (1) without hindering the electrode reaction of the redox marker (5). Specifically, they may be selected from various compounds such as short-chain alkane thiol and disulfide. Among these, 6-mercapto-1-hexanol is advantageous and preferable in that it does not hinder the redox reaction of the marker because the chain length is short, and adsorption of PNA can be avoided because of its hydrophilic terminal.

Moreover, in the method for electrochemical detection of nucleobase pair complementarity of the present invention, the single-stranded nucleic acid probe (2) may be either a DNA or a peptide nucleic acid (PNA).

PNA is a DNA analogue having neutral N-(2-aminoethyl) glycine, instead of a negatively charged phosphate, as its backbone. It is known that PNA can discriminate various mismatch DNAs in high response and has a higher binding affinity to complementary DNA than DNA (*Nature* 1993, 365, 566; *J. Chem. Soc., Chem. Commun.* 1993, 800; *Clin. Chem.* 1993, 39, 715).

For example, Wang et al. used PNA films for the detection of DNA, and reported that PNA probes deposited on carbon paste electrodes recognize complementary DNA with high selectivity (*J. Am. Chem. Soc.* 1996, 118, 7667). Further, Alinghaus et al. compared PNA and DNA probe arrays formed on solid supports, and reported that the use of PNA enables efficient discrimination or one-base mismatches (*Anal. Chem.* 1997, 69, 3747).

The present inventors have clarified, through assiduous studies, that by using PNA as a single-stranded nucleic acid probe (2), the detection sensitivity becomes higher because clearer electric signals are emitted when there is complementarity between the analyte nucleic acid (3) and the PNA, than when DNA is used (Examples of the present application) Accordingly, it may be said that PNA is preferable as the single-stranded nucleic acid probe (2).

In the method for electrochemical detection of nucleobase pair complementarity of the present invention, the solvent, concentration, pH, etc. of the solution containing the analyte single-stranded nucleic acid (3) to be contacted with the electrode are not particularly limited. It is preferable that the solution contains a phosphate buffer or the like and that the pH is approximately 7.0, suitable for incubation of nucleic acid. Further, for highly accurate detection, it is advisable that the concentration of the analyte single-stranded nucleic acid (3) is not very high, preferably in the range of $10^{-11}$ to $10^{-2}$ M.

In this method for electrochemical detection of nucleobase pair complementarity, the analyte nucleic acid (3) may be, for example, a chemically synthesized polynucleotide or oligonucleotide, or a natural nucleotide such as DNA or RNA. Thus, the method of the present invention also enables the diagnosis of genetic or viral diseases by confirming the synthesis of a nucleotide with the desired sequence from its complementarity to the probe single-stranded nucleic acid, or by confirming mutations on natural DNA through the presence or absence of complementarity to the probe single-stranded nucleic acid (2).

Further, the redox marker (5) is not particularly limited as long as it has a negative charge and does not influence the binding of the probe molecule to the electrode or the complementarity of the nucleobase pair and its electron transfer is suppressed by the complementarity of the nucleobase pair. Preferable examples include $[Mo(CN)_6]^{4-/3-}$ and $[Fe(CN)_6]^{4-/3-}$. The concentration of such a redox marker (5) is not particularly limited. For highly accurate measurement, it is preferable that the concentration is in the range of 0.1 to 1 mM for, for example, $[Fe(CN)_6]^{4-/3-}$.

The foregoing redox reaction may be detected by the electrode reaction, and its means and conditions are not particularly limited. Specifically, coulometry, Faraday impedance spectroscopy, voltammetry and the like are exemplified. Voltammetry, by which the change in redox potential can be conveniently measured in high sensitivity and which does not require complicating calculation that could cause errors, is most preferable.

In the above method for electrochemical detection of nucleobase pair complementarity, the method for preparing the modified electrode (11) in the present invention is not particularly limited as long as the binding of the single-stranded nucleic acid probe (2) to the electrode (1) is stable and separation does not occur during the electrochemical reaction of the redox marker (5) or the hybridization with the analyte nucleic acid (3). For example, known methods (*Langmuir* 1999, 15, 3703; *Anal. Chem.* 1999, 71, 394: *Anal. Chem.* 1999, 72, 1334, etc.) may be applied, or the probe single-stranded nucleic acid (2) may be chemically or physically linked to the surface of the electrode through various linkers. Preferably, as shown in the after-mentioned Examples, the single-stranded nucleic acid probe (2) and the molecule (4) that fills the space between the probe molecules and is non-complementary to the analyte nucleic acid (3), are formed on the surface of the electrode (1) as a mixed monolayer to provide the modified electrode (11).

The method for electrochemical detection of nucleobase pair complementarity of the present invention enables miniaturization by applying known microcells or by placing a plurality of such modified electrodes on a plate, and also enables simultaneous analysis of many samples using a small amount of the specimens. Further, expensive devices or the like are not required and ordinary electrochemical measuring devices such as a potentiostat can be used. Therefore, the present invention is useful as a simple method for performing highly accurate DNA diagnosis and analysis of synthesized oligonucleotides on-site in the field of medicine and industry.

Hereinafter, embodiments of the invention is described in more detail by the following Examples with reference to the attached drawings of course, it goes with out saying that this invention is not limited to the following Examples, and that there are various aspects to its details.

EXAMPLES

<Preparations>

(1) Reagents

A 10-mer PNA probe having cysteine in the end was purchased from Sawady Technology. As represented by chemical formula 1, the structure consists of a cysteine and an ethylene glycol unit linked to the 5' terminal of the oligopeptide of Sequence ID No: 1.

Sequence ID No: 2 (5'-HS(CH$_2$)$_6$-GGC AGT GCC TCA CAA-3'), a 15-mer DNA probe having a hexanethiol group at its terminal; oligonucleotides (dA)$_{10}$ and (dT)$_{10}$; the oligonucleotide of sequence ID No: 3 (5'-TTG TGA GGC ACT GCC-3'), which shows complementarity to the DNA probe; the oligonucleotide of Sequence ID No: 4 (5'-TGA GGC ACT G-3'), which shows complementarity to the PNA probe; and the oligonucleotide of Sequence ID No: 5 (5'-TGA GAC ACT G-3'), which contains one mismatch and binds to the PNA probe were all purchased from Nisshinbo Industries (Inc.).

Further, 6-mercapto-1-hexanol was purchased from Fluka AG (Buchs, Switzerland).

Other chemicals used were of analytical reagent grade.

Moreover, water deionized using a Milli-Q water system (Millipore, Bedford, Mass.) and charcoal-treated (specific resistance >18.2 MΩcm) was used in all aqueous solutions.

(2) Electrodes

Gold disk electrodes (area 1 mm$^2$, Bioanalytical Systems (BAS), West Lafayette, Ind.) were polished on a felt pad coated with alumina slurry having particle sizes of 0.3 and 0.5 μm (Alpha and Gamma Micropolish® No. 2, Buehler, Lake bluff, Ill.) for at least 10 minutes, rinsed repeatedly with water, and cleansed in a sonicator.

The polished electrodes were dipped in a 0.5 M KOH solution deoxygenated by purging with argon for 15 minutes, and scanned from −0.4 V to −1.2 V (vs. a saturated calomel electrode) until changes in cyclic voltammograms (CVs) were not observed anymore.

The DNA or PNA probes were immobilized based on the method reported by Takenaka et al. (*Anal. Chem.* 2000, 72, 1334). The electrodes were washed with water, and placed upside-down in a disposable test tube.

An aliquot of 2 μL of the 400 μM DNA or the 100 μM PNA probe (aqueous solution) was deposited onto the gold disk electrode the test cube was sealed to prevent water evaporation, and kept at room temperature for a predetermined period of time. For the preparation of mixed monolayers, the electrodes were then washed with water, and dipped in an aqueous 1 mM 6-mercapto-1-hexanol solution at room temperature for 30 minutes. Just before use, the electrodes were washed repeatedly with water.

(3) Hybridization

The electrodes were dipped into 100 μL of the oligonucleotide solution containing 0.1 M phosphate buffer (potassium salt solution, pH 7.0) and 1 M NaCl. For the DNA probe, the electrodes were incubated at 65.0±0.1° C. for 40 minutes, followed by slow cooling to room temperature. For the PNA probe, the electrodes were incubated at room temperature, 37.0±0.1° C. or 47.0±0.1° C. for 40 minutes to interact with oligonucleotides.

(1)

Nu: Sequence ID No: 1

(4) Electrochemical Measurement

All electrochemical measurements were performed with a CV-50 W electrochemical analyzer (BAS) at room temperature with a three-electrode configuration on solutions deoxygenated by purging with argon gas for 15 minutes. All potentials were measured versus the Ag/AgCl electrode, and a platinum wire was used as the auxiliary electrode. Cyclic voltammetry was performed in 0.1 M phosphate buffer solutions (potassium salt, pH 7.0) containing 0.5 mM $K_4[Fe(CN)_6]$ and 0.5 mM $K_3[Fe(CN)_6]$ as an electrochemically active marker. The potential was scanned from 0 mV to +500 mV and again back to 0 mV. The scan rate was 1003 mV/s.

The first CV was analyzed, and the relationship between the DNA concentration and the sensor response was measured from the current value at 101 mV (peak potential for $[Fe(CN)_6]^{4-/3-}$ when analyte DNA was absent).

Example 1

Single-Stranded DNA Modified Gold Electrodes

Figure 2:
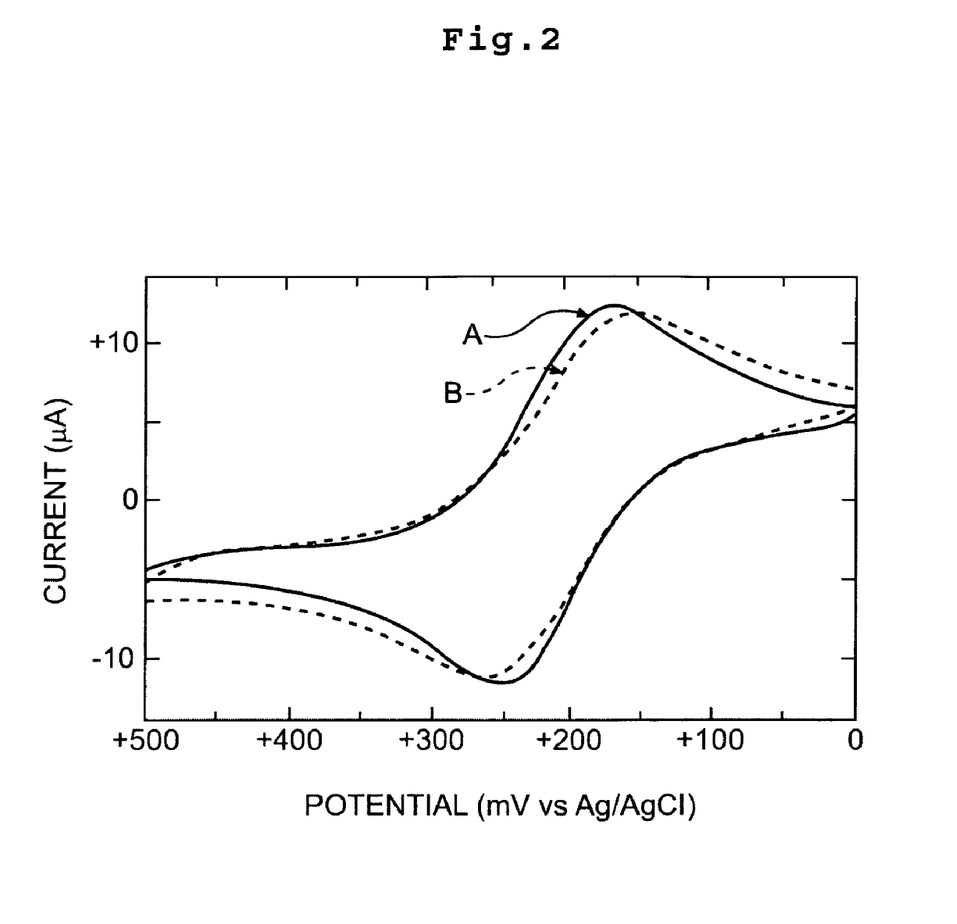
FIG. 2 is a cyclic voltammogram showing redox reactions of $[Fe(CN)_6]^{4-/3-}$ when a modified electrode having a monolayer of single-stranded DNA as a probe is used in Examples of the present invention (A: single-stranded DNA modified gold electrode, B: single-stranded DNA modified gold electrode+analyte single-stranded nucleic acid).

The electrodes polished by the foregoing method were modified with the 15-mer single-stranded DNA probe for 35 hours. A CV of $[Fe(CN)_6]^{4-/3-}$ measured using this electrode is shown in FIG. 2A.

The redox was nearly reversible, and peak separation $\Delta E_p$ was 75 mV. $\Delta E_p$ was larger than that for the bare electrode, indicating that the redox reaction of $[Fe(CN)_6]^{4-/3-}$ was slightly inhibited by the negative charge on the surface of the single-stranded DNA probe.

(A similar result was reported by Patolsky et al. for a modified electrode with a 18-mer oligonucleotide (20 μM, 10 hours) linked to the gold surface (*Langmuir* 1999, 15, 3703)).

Next, the electrodes modified with the 15-mer DNA probe were dipped in a 88 μM solution of an analyte single-stranded DNA, and incubated in a water bath at 65.0° C. for 40 minutes, followed by slow cooling to room temperature. This incubation temperature was determined based on the melting temperature of the single-stranded DNA probe (61.0° C. according to *Methods in Enzymology Vol.* 168, Academic Press, San Diego, Calif., 1989, p. 761).

The CV shown in FIG. 2B indicated that $\Delta E_p$ was 93 mV and that it was increased by 18 mV through hybridization.

Example 2

Single-Stranded PNA Modified Gold Electrodes

From Example 1, it was indicated that even when the single-stranded DNA is used as a probe, the hybridization can sufficiently be confirmed from the change in $\Delta E_p$ in the CV.

However, it is considered that since the single-stranded DNA has a large number of negative charges, repulsion between the probe molecules hinders their self-assembly and defects tend to occur in the monolayer on the electrode surface. It is further considered that since a large number of negative charges are present on the surface of the single-stranded DNA, the change in charge on the probe surface by hybridization is hard to detect.

Meanwhile, since PNA is neutral, the change in charge of the probe surface by hybridization is expected to be great.

Accordingly, the electrodes polished by the foregoing method were modified with a 10-mer single-stranded PNA for 24 hours to form modified electrodes.

Figure 3:
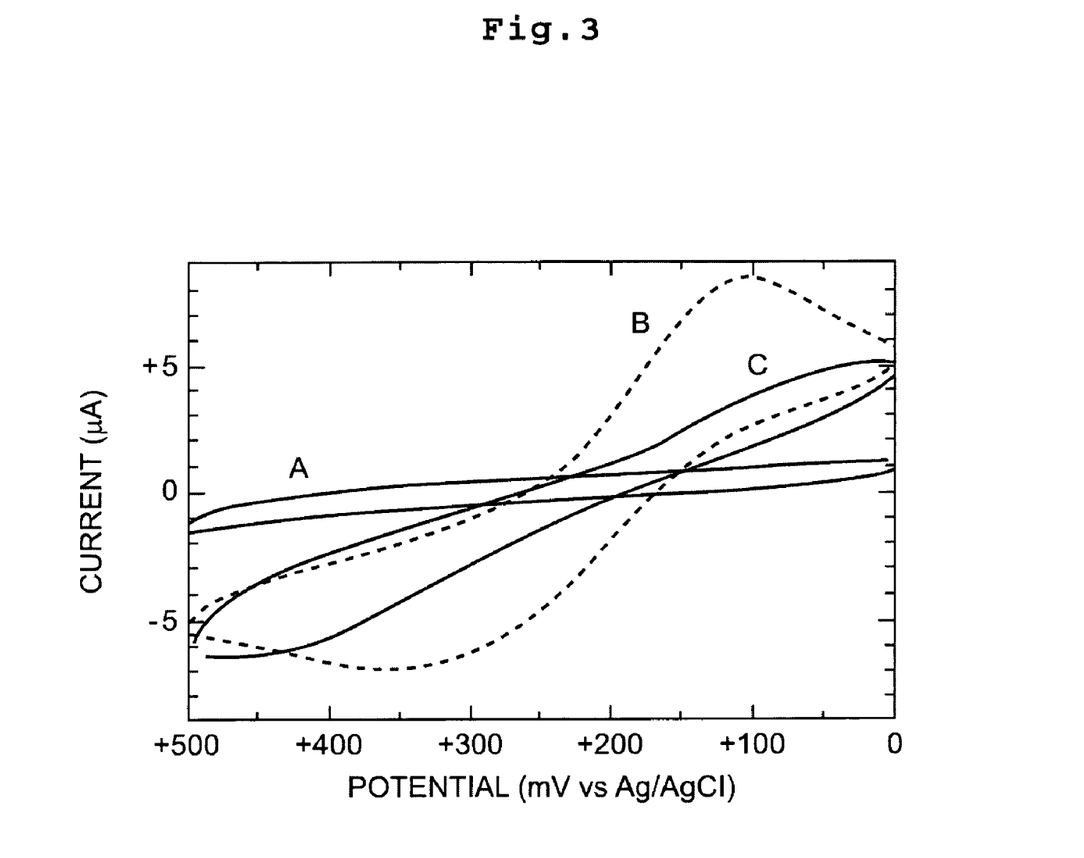
FIG. 3 is a cyclic voltammogram showing redox reactions of $[Fe(CN)_6]^{4-/3-}$ when a modified electrode having a monolayer of single-stranded PNA as a probe is used in Examples of the present invention (A: single-stranded PNA (24 hours) modified gold electrode. B: single-stranded PNA (0.5 hour)+6-mercapto-1-hexanol (0.5 hour) modified electrode (hereinafter referred to as PNA mixture modified gold electrode), C: PNA mixture modified gold electrode+analyte single-stranded nucleic acid).

FIG. 3A shows the CV for the measurement of $[Fe(CN)_6]^{4-/3-}$ redox, using this electrode. The result indicates that the electron transfer between the redox marker and the electrode was totally suppressed. This is presumably due to the self-assembled monolayers (SAMs) being very tight.

Thus, in order to make the SAMs more permeable, attempts were made to shorten the time of modification with the single-stranded PNA solution and to widen the molecular space between the PNA single strands. Further, to prevent the PNA single strands from lying down and inhibit hybridization with the analyte single-stranded DNA, voids between the PNA single strands were filled with 6-mercapto-1-hexanol.

Example 3

Formation of PNA Mixture Modified Gold Electrodes

The electrodes were contacted with the PNA single strand solution for 30 minutes, and then contacted with the 1 mM 6-mercapto-1-hexanol solution for 30 minutes. FIG. 3B shows the CV of $[Fe(CN)_6]^{4-/3-}$ measured using a gold electrode modified with this mixed monolayer.

The CV in FIG. 3B was quasi-reversible ($\Delta E_p=265$), indicating that the electron transfer of $[Fe(CN)_6]^{4-/3-}$ was less hindered than when the single-stranded PNA modified gold electrode was used in Example 2.

Accordingly, only the electrodes modified with PNA mixture modified gold electrodes were used hereinafter.

Example 4

Hybridization with the Analyte (Oligonucleotide)

The single-stranded PNA modified electrodes were incubated at 47° C. in a solution of 10-mer DNA (100 μM), which showed complementarity to the PNA single strand for 40 minutes, and washed with water, followed by the electrochemical measurement. This incubation temperature was determined from an estimated value of $T_m$. It is known that $T_m$ increases by 1° C. (*Bioorg. Ned. Chem.* 1996, 4, 5) or 1.5° C. (*Nature* 1993, 365, 566) per PNA/DNA base pair in comparison with the $T_m$ of a DNA/DNA duplex with the same sequence. Since the corresponding $T_m$ of DNA/DNA duplex is 38.5° C., the $T_m$ of the PNA/DNA duplex was estimated to be 48.5° or 53.5° C.

The CV of $[Fe(CN)_6]^{4-/3-}$ after the PNA single strand of the gold electrode modified with the mixed monolayer was hybridized with the 10-mer DNA, is shown in FIG. 3C. The CV of $[Fe(CN)_6]^{4-/3-}$ for the PNA/DNA modified electrode was found to be irreversible. No peak was confirmed, indicating that the electron transfer between $[Fe(CN)_6]^{4-/3-}$ and the electrode was efficiently inhibited.

From this result, it was confirmed that the 10-mer DNA was hybridized to the single-stranded PNA probe. While the PNA probe has a neutral backbone, the PNA/DNA duplex provides the modified electrode surface with negative charges ($10e^-$ (=−10) per PNA probe). It was suggested that with the electrostatic repulsion of the negative charges from the PNA/DNA duplexes on the modified electrode, $[Fe(CN)_6]^{4-/3-}$ could not easily access the electrode surface, and the redox reaction was inhibited.

Figure 4:
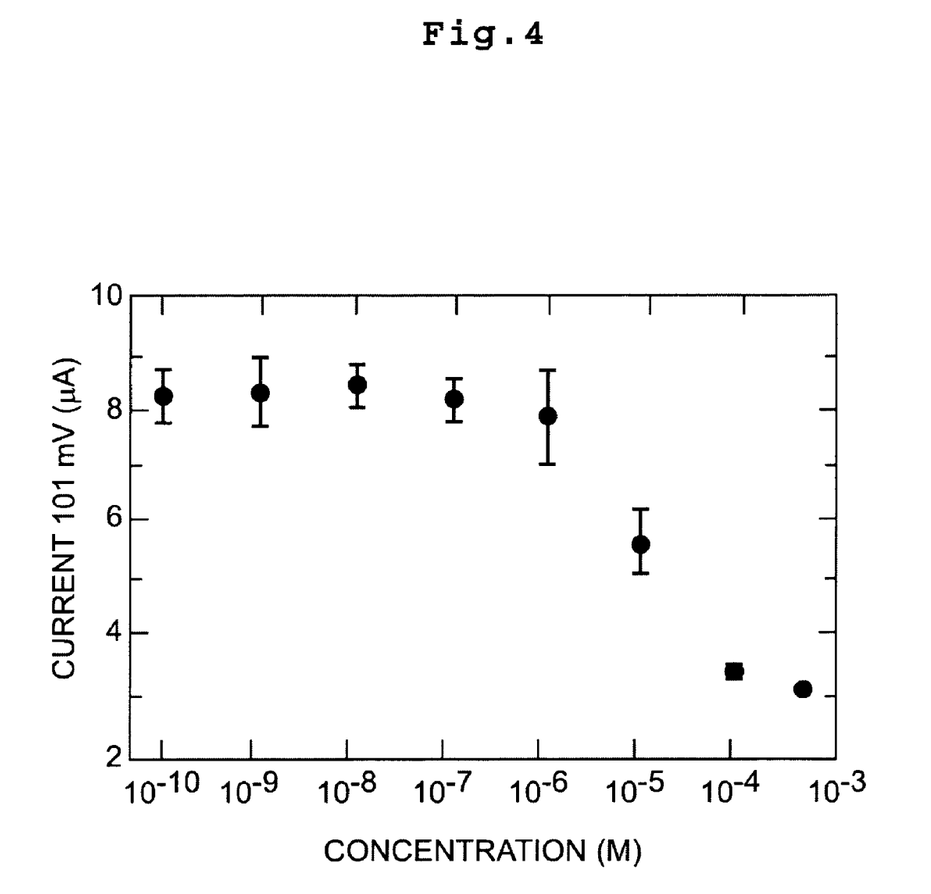
FIG. 4 is a graph showing the relationship between the concentration of the analyte single strand and the reduction current of $[Fe(CN)_6]^{4-/3-}$ at +101 mV when a PNA mixture modified gold electrode is used.

FIG. 4 in a graph showing the relationship between the electrode reaction (current value at +101 mV) and the concentration of the analyte DNA. It was confirmed that in the DNA concentration range from $10^{-10}$ M to $10^{-7}$ M, the current value remained unchanged, whereas it decreased between $10^{-6}$ M to $10^{-4}$ M. At higher concentrations, it reached the lowest value, suggesting that nearly all of the single-stranded PNA probes on the electrode were hybridized to the analyte DNA, and saturated.

In view of the foregoing, it was indicated that the 10-mer single-stranded DNA could be detected at a micromolar level by CV measurement using the PNA mixture modified gold electrode. Further, by applying an electrochemical measurement method with higher accuracy, such as pulse voltammetry, the measurement limit for the. modified electrode can be expected to improve.

Example 5

Selective Detection of Oligonucleotides

In order to confirm the analyte (oligonucleotide) selectivity of the PNA mixture modified gold electrodes prepared in FIG. 3, the hybridization and the measurement were performed in the same manner as in Example 4 using an oligonucleotide that is non-complementary to the PNA single strand used.

Figure 5:
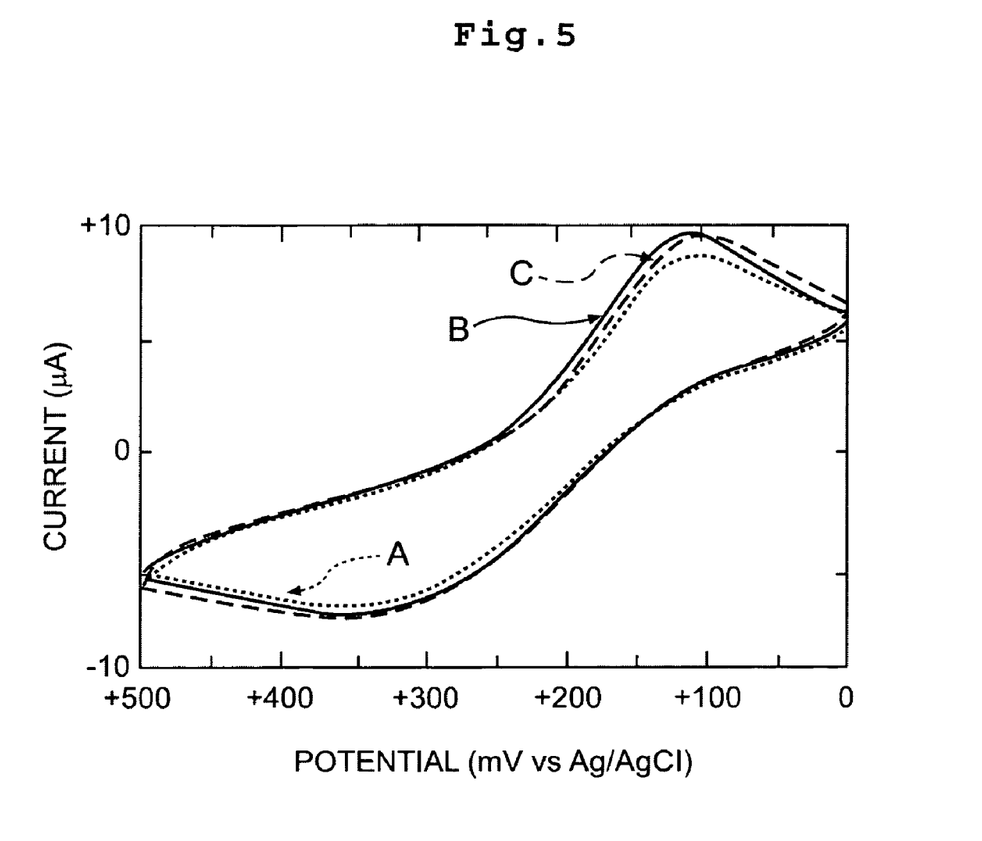
FIG. 5 is a cyclic voltammogram showing the redox reaction of $[Fe(CN)_6]^{4-/3-}$ when the PNA mixture modified gold electrode is used in Examples of the present invention, performed to confirm the selectivity of the analyte single strand (A: PNA mixture modified gold electrode, B: PNA mixture modified gold electrode+40 μM $(dA)_{10}$, C: PNA mixture modified gold electrode+100 μM $(dT)_{10}$).

FIGS. 5B and 5C show the CVs measured using a PNA mixture modified gold electrode incubated at room temperature in a 40 µM $(dA)_{10}$ solution and a 100 µM $(dT)_{10}$ solution using $[Fe(CN)_6]^{4-/3-}$ as a redox marker.

The incubation was performed at room temperature which was more advantageous for the DNA binding than at 47.0° C. used in Example 4, and even though the concentration of the analyte (non-complementary DNA) was higher than the concentration of the analyte (complementary DNA) in Example 4, the redox reaction of $[Fe(CN)_6]^{4-/3-}$ remained almost unchanged as compared to when the electrode before the incubation was used (FIG. 5A).

It was therefore indicated that these oligonucleotides did not hybridize with the PNA single strand probe.

Figure 6:
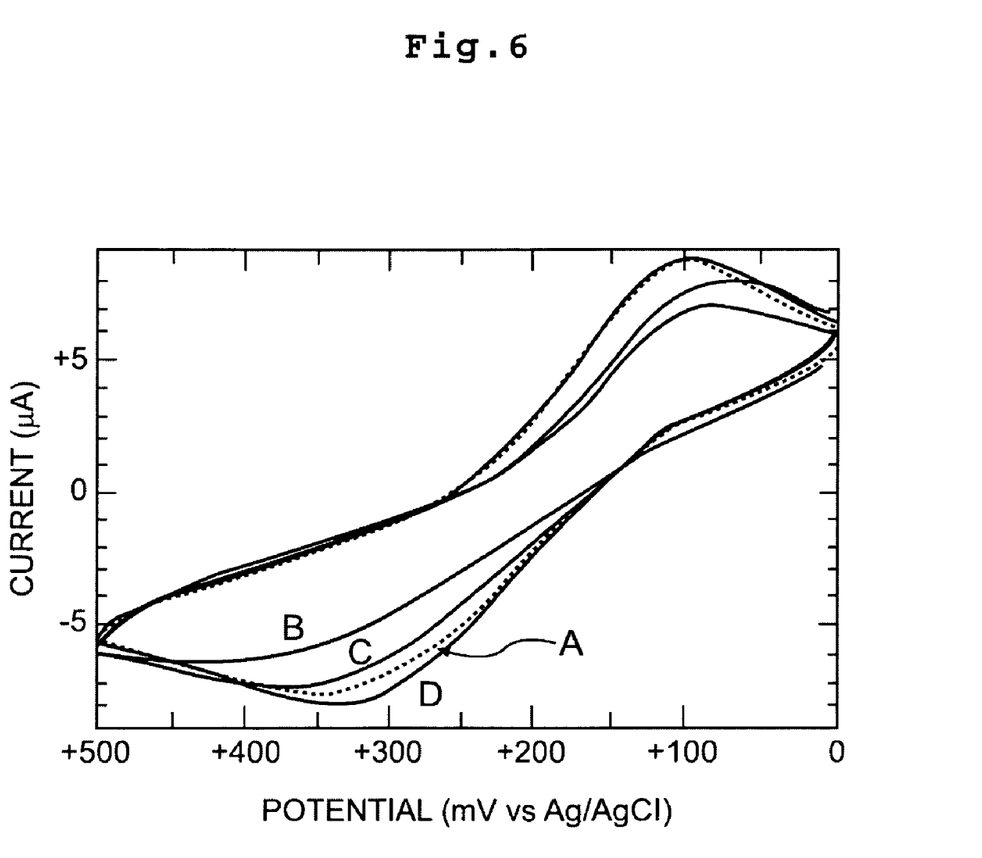
FIG. 6 is a cyclic voltammogram showing the redox reaction of $[Fe(CN)_6]^{4-/3-}$ when the PNA mixture modified gold electrode is used in Examples of the present invention, performed to examine the selectivity of the analyte single-stranded nucleic acid. (A: PNA mixture modified gold electrode, B: PNA mixture modified gold electrode+100 μM one-base mismatch oligonucleotide (room temperature), C: PNA mixture modified gold electrode+100 μM one-base mismatch oligonucleotide (37.0° C.), D: PNA mixture modified gold electrode+100 μM one-base mismatch oligonucleotide (47.0° C.)).

Moreover, in order to confirm the selectivity of the modified electrode, the same measurement was performed using oligonucleotides having a one-base mismatch The CVs for the PNA mixture modified gold electrode obtained by incubating a 100 µM solution of a one-base mismatch oligonucleotide at room temperature, 37.0° C. and 47.0° C. respectively, measured using $[Fe(CN)_6]^{4-/3-}$ as a redox marker, are shown in FIGS. 6B, 6C and 6D. The CV for the electrode obtained by incubation at room temperature showed a quasi-reversible CV ($\Delta E_p$=360 mV), indicating that the mismatch oligonucleotide was weakly bound to the PNA single strand probe. However, the $\Delta E_p$ decreased for those obtained under higher incubation temperatures. $\Delta E_p$: 309 mV (37.0° C.), 252 mV (47.0° C.).

The $\Delta E_p$ of the modified electrode incubated at 47.0° C. was equal to that of the electrodes incubated in solutions of $(dA)_{10}$ and $(dT)_{10}$. This indicated that the PNA mixture modified gold electrodes could also distinguish non-complementary oligonucleotides that differ from the target DNA only by a mismatch of one base.

Industrially Applicability

As has been described in detail above, the present invention provides a simple, highly applicable method for the electrochemical measurement of nucleobase pair complementarity, that can even detect a mismatch of one nucleotide base in high accuracy. By using the method of the present invention, sequences or mutations of various nucleic acids can easily be determined in high accuracy. Further, the use of the modified electrode of the present invention enables miniaturization of the nucleobase pair complementarity measuring device, and also enables the simultaneous measurement of nucleobase pair complementarity for many samples using only a small amount of the specimens.

The invention claimed is:

1. A method for electrochemical detection of nucleobase pair complementarity, which comprises:
   contacting a modified electrode obtained by bonding at least a single stranded nucleic acid to an electrode so that the single-stranded nucleic acid is oriented vertically with respect to the surface of the electrode and the electrode is a gold electrode, with a solution containing an analyte single stranded nucleic acid and a redox marker, wherein the redox marker is $[Mo(CN)_6]^{4/13-}$ or $[Fe(CN)_6]^{4/13-}$; and
   detecting the disappearance of an electric signal generated by reaction between the modified electrode and the redox marker, when the single stranded nucleic acid on the modified electrode and the analyte single stranded nucleic acid are complementary.

2. The method for electrochemical detection of nucleobase pair complementarity of claim 1, wherein the electrode is a gold disk electrode.

3. The method for electrochemical detection of nucleobase pair complementarity of claim 1, wherein a molecule that is not complementary to the analyte single stranded nucleic acid is bonded to the modified electrode along with the single stranded nucleic acid for vertically orienting the single stranded nucleic acid with respect to the surface of the electrode.

4. The method for electrochemical detection of nucleobase pair complementarity of claim 3, wherein the single stranded nucleic acid and the molecule that is not complementary to the analyte single stranded nucleic acid form a mixed monolayer on the surface of the electrode.

5. The method for electrochemical detection of nucleobase pair complementarity of claim 3, wherein the molecule that is not complementary to the analyte single stranded nucleic acid is 6-mercapto-1-hexanol.

6. The method for electrochemical detection of nucleobase pair complementarity of claim 1, wherein the single stranded nucleic acid is a single stranded peptide nucleic acid.

7. The method for electrochemical detection of nucleobase pair complementarity of claim 1, wherein the concentration of the analyte single stranded nucleic acid is $10^{-11}$ to $10^{-2}$ M.

8. The method for electrochemical detection of nucleobase pair complementarity of claim 1, wherein the analyte single stranded nucleic acid is a single stranded DNA.

9. The method for electrochemical detection of nucleobase pair complementarity of claim 1, wherein the redox marker is $[Fe(CN)_6]^{4-/3-}$.

10. The method for electrochemical detection of nucleobase pair complementarity of claim 9, wherein the concentration of $[Fe(CN)_6]^{4-/3-}$ is 0.1 to 1 mM.

11. The method for electrochemical detection of nucleobase pair complementarity of claim 1, wherein the redox reaction is measured by voltammetry.

12. A modified electrode for detecting nucleobase pair complementarity by the method of claim 1, which comprises a mixed monolayer of a peptide nucleic acid and a molecule that is not complementary to the analyte nucleic acid, formed on the surface of a gold disk electrode.

* * * * *